US005961503A

United States Patent [19]

[11] Patent Number: 5,961,503

Simmet et al.

[45] Date of Patent: Oct. 5, 1999

[54] BOAR SEMEN COLLECTION BAG

[75] Inventors: Ludwig O. Simmet, Verona, Wis.; Christian J. Simmet, Landshut, Germany

[73] Assignee: Minitube of America, Inc., Verona, Wis.

[21] Appl. No.: 09/078,168

[22] Filed: May 13, 1998

[51] Int. Cl.$^{6}$ ...................................................... A61F 5/453

[52] U.S. Cl. ............................................ 604/349; 604/347

[58] Field of Search ..................................... 604/906, 349, 604/347, 327; 600/38

[56] References Cited

U.S. PATENT DOCUMENTS 3,539,012 11/1970 MacNeil .
3,744,639 7/1973 Teeple, Jr. et al. .
4,439,319 3/1984 Rock .
4,620,531 11/1986 Dyer .
4,690,678 9/1987 Douglas-Hamilton .................. 604/349
4,744,352 5/1988 Emery .
4,983,286 1/1991 Inagaki et al. .
5,368,583 11/1994 Fleury .
5,540,670 7/1996 Lindholm-Ventola .
5,569,225 10/1996 Fleury .

*Primary Examiner*—John G. Weiss
*Assistant Examiner*—Catherine Cogut
*Attorney, Agent, or Firm*—Lathrop & Clark LLP

[57] ABSTRACT

Two flat segments of flexible plastic are sealed along the edges and at the bottom, to present an upwardly opening bag. A rectangular sheet of filter material is folded to form a filter pouch and positioned within the collapsed collection bag, with the upper edges of the folded filter material halves fused to opposing sides of the bag above a perforation or line of weakened material. When the bag is disposed within a collection mug, the upper portions of the bag extend as a shroud around the exterior of the mug, and the filter material is stretched out across the opening to the bag. A boar's penis is directed to ejaculate into the mug, and the ejaculate gel plug is retained on the filter material, while the semen passes through the filter material into the collection bag. When collection is complete, the shroud and the attached filter material are separated from the collection bag and disposed of.

13 Claims, 3 Drawing Sheets

BOAR SEMEN COLLECTION BAG

FIELD OF THE INVENTION

The present invention relates to equipment in support of animal artificial insemination in general, and to apparatus for collecting boar semen in particular.

BACKGROUND OF THE INVENTION

As with all fields of modern commerce, agricultural production increasingly places a premium on efficient use of resources and productivity of investment. Mechanical advancements in plowing, seeding, and harvesting machinery have for decades contributed to increasing yields of plant crops. Although the active employment of similar productivity enhancing technology in animal crops has trailed plant culture automation, such advancements are now spreading to meat producers.

The culture of pigs for slaughter has particularly demanding economics. In order to maximize the crop of piglets, a producer seeks to have as few boar for the number of fertile sows as possible. A boar is capable of producing on average sufficient semen to artificially inseminate 15 sows twice a week, although a boar is only capable of inseminating two sows a week through mating. In a traditional practice, the sows to be inseminated are aligned for service by a boar, and are inseminated twice. Because a litter of as many as 12 piglets is desirable, it is important that each sow receive sufficient semen. Hence, in practice, a pork producer must retain many more boar than is optimal. Furthermore, the actual coupling of the boar with the sows requires additional labor for supervision which adds to the overall cost of the pigs produced.

Artificial insemination (AI) technology has made it possible to collect semen from a boar without contact with the sow, and to then inseminate each sow with a controlled and tested quantity of semen in an isolated environment. With modern AI techniques, a 1,000 sow herd can be adequately handled with only three to four boars.

The economic benefits of AI are well recognized. Nevertheless, the biological processes involved place demanding burdens on the practitioners. Unlike plant culture, in which seeds and seedlings are naturally adapted to survive in inclement weather and dirty conditions, AI products must be collected, treated, and transported under hygienic conditions and at controlled temperatures.

The collection of the boar semen itself is at present far from automated. An agricultural worker must lead the boar into the collection area and induce the animal to mount a simulated sow or collection dummy. Once ejaculation begins, the worker positions a plastic bag, retained in an insulated mug, to receive the ejaculate. Because only a single worker is involved, one hand manipulates the boar's penis to ejaculate into the mug, while the other hand maneuvers the mug to receive the biological material. The collection is further complicated by the fact that fluids present on the prepuce of the boar's penis are toxic to the semen. Hence it is important that they not contaminate the collected semen.

Because the boar ejaculate contains a gel plug fraction, it is necessary to filter this more viscous fraction from the semen. In conventional collection practices, a sheet of filter paper or gauze material was positioned over the opening to the mug and held in place with a rubber band. The operation of positioning and securing the filter required some manual dexterity and skill, and presented many opportunities for contamination of the semen both during collection and during separation of the filter from the collection bag.

What is needed is a boar semen collection bag which is easier to install in the collection mug, and which is conducive to hygienic collection practices to facilitate collection of semen of optimum quality.

SUMMARY OF THE INVENTION

The boar semen collection bag of this invention is formed with an expandable filter, which is interposed in the ejaculate stream by installing the bag in a collection mug. The hygienic bag is comprised of two flat segments of flexible plastic sealed along the edges and at the bottom, so the top is open. A rectangular sheet of filter material is folded and formed into a filter pouch which is positioned within the collapsed collection bag, with the upper edges of the folded filter material halves fused to opposing sides of the bag above a perforation or line of weakened material. When the bag is disposed within a collection mug, the upper portions of the bag extend as a shroud around the exterior of the mug, and the filter material is stretched out across the opening to the bag. The boar's penis is directed to ejaculate into the mug, and the ejaculate gel plug is retained in the filter pouch, while the semen passes through the filter material into the collection bag. When collection is complete, the shroud and the attached filter material are separated from the collection bag and disposed of, thereby preserving the semen from contact with the boar prepuce and the gel plug.

It is an object of the present invention to provide a collection bag for boar semen which is easy to install within a collection mug.

It is an additional object of the present invention to provide a collection bag for boar semen which may be installed within a collection mug without contact with the installer's hands to preserve a hygienic contact surface on the interior of the bag.

It is another object of the present invention to provide a collection bag for boar semen which prevents the commingling of undesirable ejaculate fractions with the collected semen.

It is a further object of the present invention to provide a collection bag for boar semen which automatically positions a filter above the collecting portion of the bag when the bag is installed within a collection mug.

It is also an object of the present invention to provide a collection bag for boar semen which shields the bag interior and the filter material from contamination prior to collecting the semen.

It is an additional object of the present invention to provide a bag which can be used for both collection of boar semen and for the processing, bulk storage, and dispensing thereof.

It is yet another object of the present invention to provide a boar semen collection bag which may contain and transport the collected semen from time of collection to final dispensing into the final semen bottles.

It is a further object of the present invention to provide a device for collecting boar semen which permits the collected semen to be mixed with extender and dispensed into smaller containers without having to be transferred to any intermediate container.

Further objects, features and advantages of the invention will be apparent from the following detailed description when taken in conjunction with the accompanying drawings.

DESCRIPTION OF THE PREFERRED EMBODIMENTS

Figure 1:
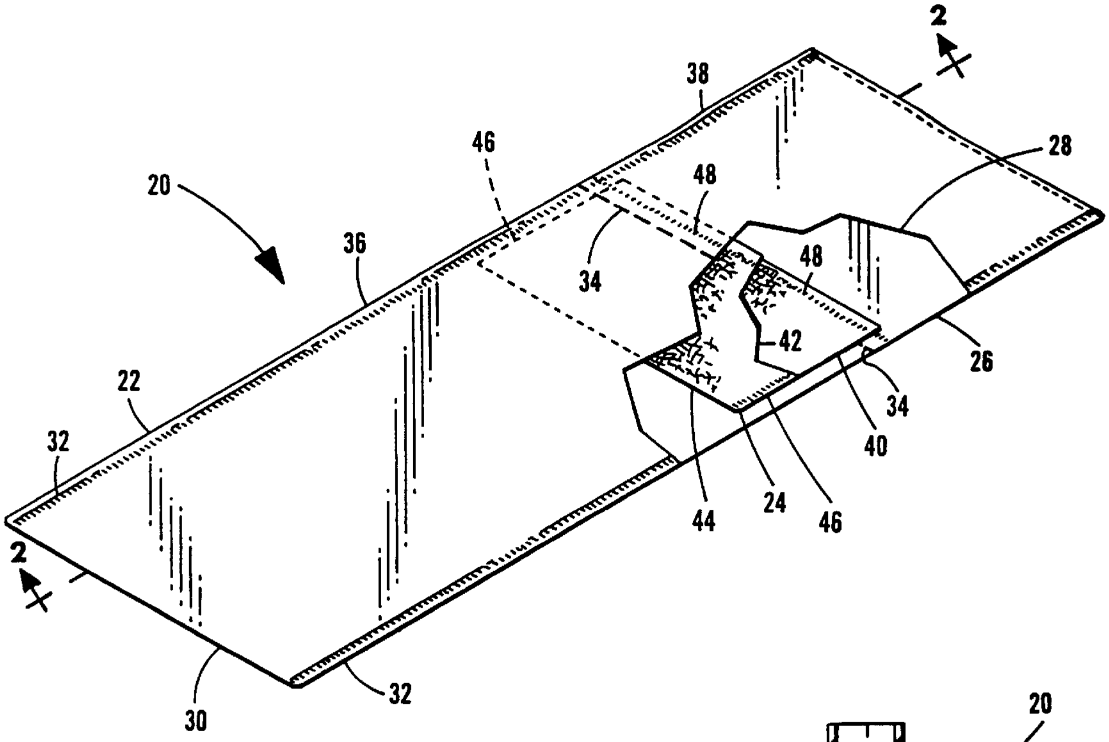
FIG. 1 is an isometric view of an unexpanded boar semen collection bag of this invention, partially broken away in section.
Figure 2:
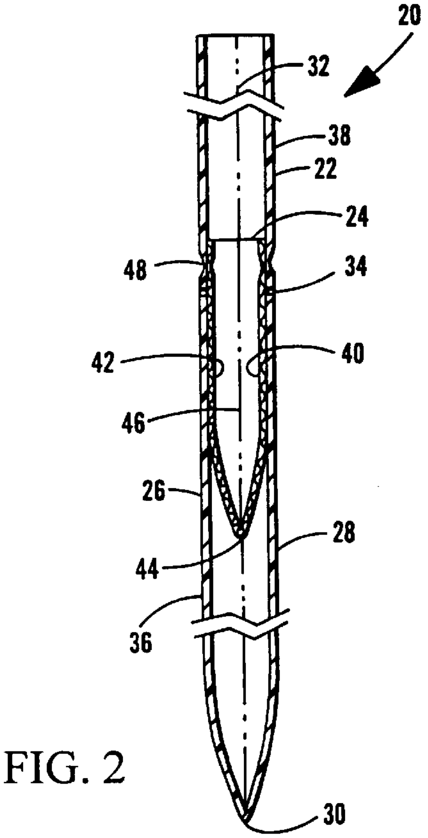
FIG. 2 is a cross-sectional view of the boar semen collection bag of FIG. 1 taken along section line 2—2.

Referring more particularly to FIGS. 1–5, wherein like numbers refer to similar parts, a boar semen collection bag 20 of this invention is shown in FIG. 1. The bag 20 is assembled from two elements, an outer container 22 formed of fluid tight plastic material, and an inner filter element 24 formed of a material which permits boar semen to pass through to be retained within the container. The container 22 may be formed of any flexible imperforate plastic material which is nontoxic to boar semen, for example, polypropylene. To facilitate handling and analysis of the bag contents, the container 22 is preferably formed of transparent plastic material. The filter element 24 may be fabricated from spunbonded olefin material such as TYVEK® material manufactured by Du Pont TYVEK, P.O. Box 80,705, Wilmington, Del. 19880-0705. The material may or may not be pin perforated. Appropriate materials are also available from Amoco, for example RFX® nonwoven fabric. The filter element 24 is preferably of a material such as high density polyethylene (HDPE) which is readily heat sealed to the polypropylene container 22.

The container 22 is an upwardly opening bag composed of a first rectangular segment 26 which overlies a second rectangular segment 28. The segments 26, 28 are connected together along the bottom and the two sides of the bag. The bottom seam 30 is preferably formed by folding a single sheet of plastic material to overlie two like dimensioned segments one on top of the other. Alternatively, the bottom seam 30 may be formed by heat sealing the two segments 26, 28, or the two segments by be opposite sides of an extruded tubular plastic component. As shown in FIG. 1, the side seams 32 are formed by heat sealing the two segments.

The container 22 is divided into two portions by a region of weakened material 34 which encircles the bag and extends generally perpendicularly to the side seams 32 and parallel to the bottom seam. The region of weakened material 34 is preferably a line of perforations through the plastic material of the container 22, but may be formed by other mechanical, thermomechanical, or chemical treatments of the container. The region of weakened material 34 defines a line of separation which divides the bag into a collection portion 36 which extends downwardly from the perforated line 34 and a disposable portion 38 which extends upwardly from the line 34. The region of weakened material 34 permits the disposable portion 38 with attached filter pouch to be separated from the collection portion 36.

The filter element 24 is positioned within the container 22 and is fastened to the disposable portion of the bag upwardly of the region of weakened material 34. The filter element 24 is preferably a single sheet of material which is folded into a first rectangular section 40 and a second rectangular section 42 along a bottom fold line 44. The filter element sections 40, 42 are heat sealed to one another along side seams 46 to form a filter pouch. The upper edges of the filter element rectangular sections 40, 42 are attached to the disposable portion 38 of the container 22 at upper attachment lines 48, such that each section of the filter element 24 is sealed to an overlying segment of the container at a position above the region of weakened material 34.

Figure 3:
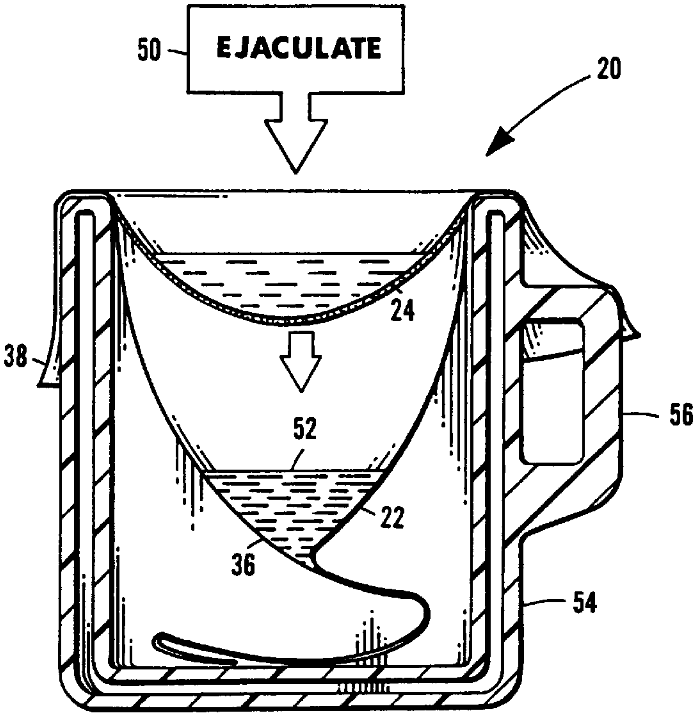
FIG. 3 is a cross-sectional view of the boar semen collection bag of FIG. 1 installed within a collection mug and receiving the components of boar ejaculate.

The bag 20 is extendable from a first flattened condition, as shown in FIG. 1, in which the filter element 24 extends substantially parallel to the bag first segment 26 and the bag second segment 28, and a collection condition, as shown in FIG. 3, in which the bag is spread such that the filter element material extends inwardly from the bag first segment and the bag second segment, such that boar ejaculate 50 may be received on the filter material, while boar semen 52 passes through the filter element 24 to be received within the collection portion 36 of the bag.

In practice, the bag 20 is installed within a collection mug 54 having a handle 56. The mug is preferably insulated to protect the contents from ambient temperatures. The bag 20 may be about 28 inches long, and preferably has a collection volume which is significantly larger than the volume of a single ejaculation, such that the collection bag may also serve to receive an extender for achieving an increased volume of semen and extender mixture. As shown in FIG. 3, the bag 20 is folded to be received within the mug 54, and the disposable portion 38 is positioned to extend downwardly around the outside of the mug. The disposable portion 38 is tugged downwardly to extend the filter element 24 across the opening of the mug 54. The disposable portion 38 serves several purposes. First, it mechanically retains the bag 20 in the mug, and prevents it from collapsing as it receives fluid contents. Second the disposable portion keeps the filter element 24 at the entrance to the mug with the maximum surface area exposed. This disposable portion also serves to protect the collection mug from contamination during the collection process. This protective feature permits the same collection mug to be used with multiple boars without sterilization of that mug between collections.

Once the boar is positioned in the semen collection facility and induced to ejaculate, the ejaculate fluid is directed into the mug with the bag installed therein. Although the collection facility will be regularly cleaned, it is an animal-occupied structure, and as such will have a level of dirt and animal products from which it is desirable to protect the collected semen. The filter element 24 and the disposable portion 38 of the bag 20 will come in contact with this undesirable environmental material, but will for the most part prevent this material from migrating into the collection portion of the bag.

Figure 4:
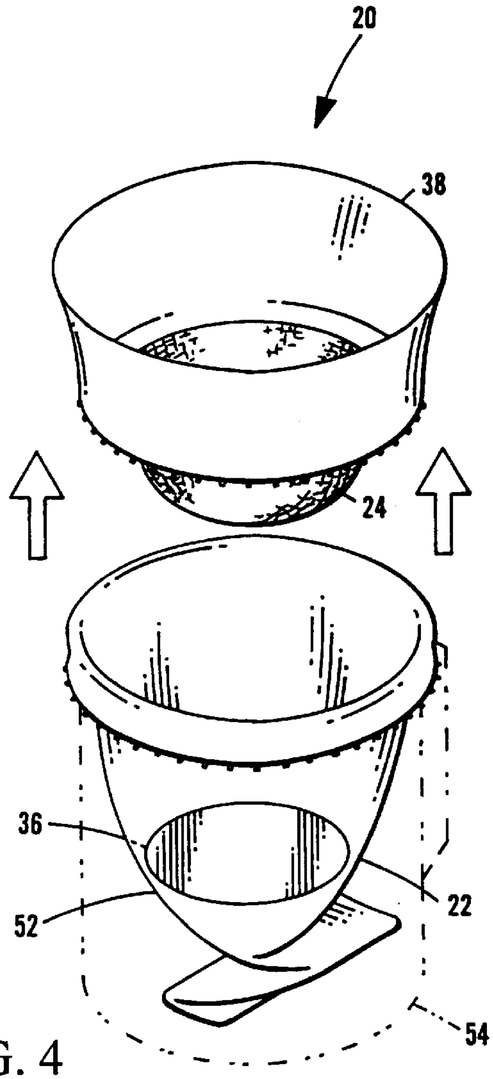
FIG. 4 is an exploded isometric view of the discarded filter and shroud portions of the collection bag being removed from the collection portion of the bag of FIG. 1.

Once the ejaculation is complete, the collection mug 54 is removed from the boar. As shown in FIG. 4, the disposable portion 38 of the bag is folded upwardly to extend away from the mug. The disposable portion 38 may be gathered together above the filter element 24 to lift the bag from the mug so that the collection portion may be grasped and the disposable portion with the attached filter and uncollected ejaculate component may be separated from the collection portion of the bag and the contained semen component. The disposable portion, filter element and uncollected component may then be disposed of in an appropriate waste facility. The collection portion of the bag may then be passed out of the collection facility to a semen processing area.

The collection bag 20 thus provides for rapid installation of the bag within the collection mug, eliminating any need to separately attach a filter element. In addition, because no manual manipulation of the filter pouch is required, the hygienic condition of the collection bag surfaces which come into contact with the semen is preserved. In addition, the filter and waste ejaculate material may be removed from the bag without contacting the collector's hands.

The collection bag 20 may be manufactured through any appropriate manufacturing steps. For example, the filter element may be first assembled by taking a sheet of filter material as it comes off a roll and extends across a trough which causes the material to fold along the bottom seam to form the two filter sections 40, 42. An electric eye detects when sufficient material has passes across the trough to form a filter element, and the side seams are heat sealed. In a similar manner, the plastic for the container 22 is unrolled across a trough to form the two bag segments, and the side seams of the bag are formed by applying heat to the adjacent edges of the plastic segments. Alternatively, the collection bag can be formed from a tubular roll of plastic material, which is sealed along the bottom edge.

The filter element is connected to the bag by placing a paperboard, aluminum or similar card within the folded filter pouch and positioning at the appropriate depth within the assembled bag and applying a heat sealing tool to the exterior of both sides of the bag at a position above the region of weakened material. The paperboard card prevents the two sections of the filter element from being fused to one another when the filter element is fused to the bag. The card also serves as a spacer or positioning device for properly positioning the filter pouch within the bag.

The collection bag 20 thus provides several advantages. It minimizes contamination of the collected semen, does not require the filter to be handled in setup, and permits the semen to be collected and processed, stored and dispensed in the same container. The filter element provides for high flow rate of semen.

In a medium to large scale collection operation, where the size of the facility justifies the capital investment, the neat semen, after collection, is processed further with the assistance of automated equipment. For example, a packaging apparatus receives the collection bag and automatically transfers the semen which has been extended with a culture medium into smaller containers.

Figure 5:
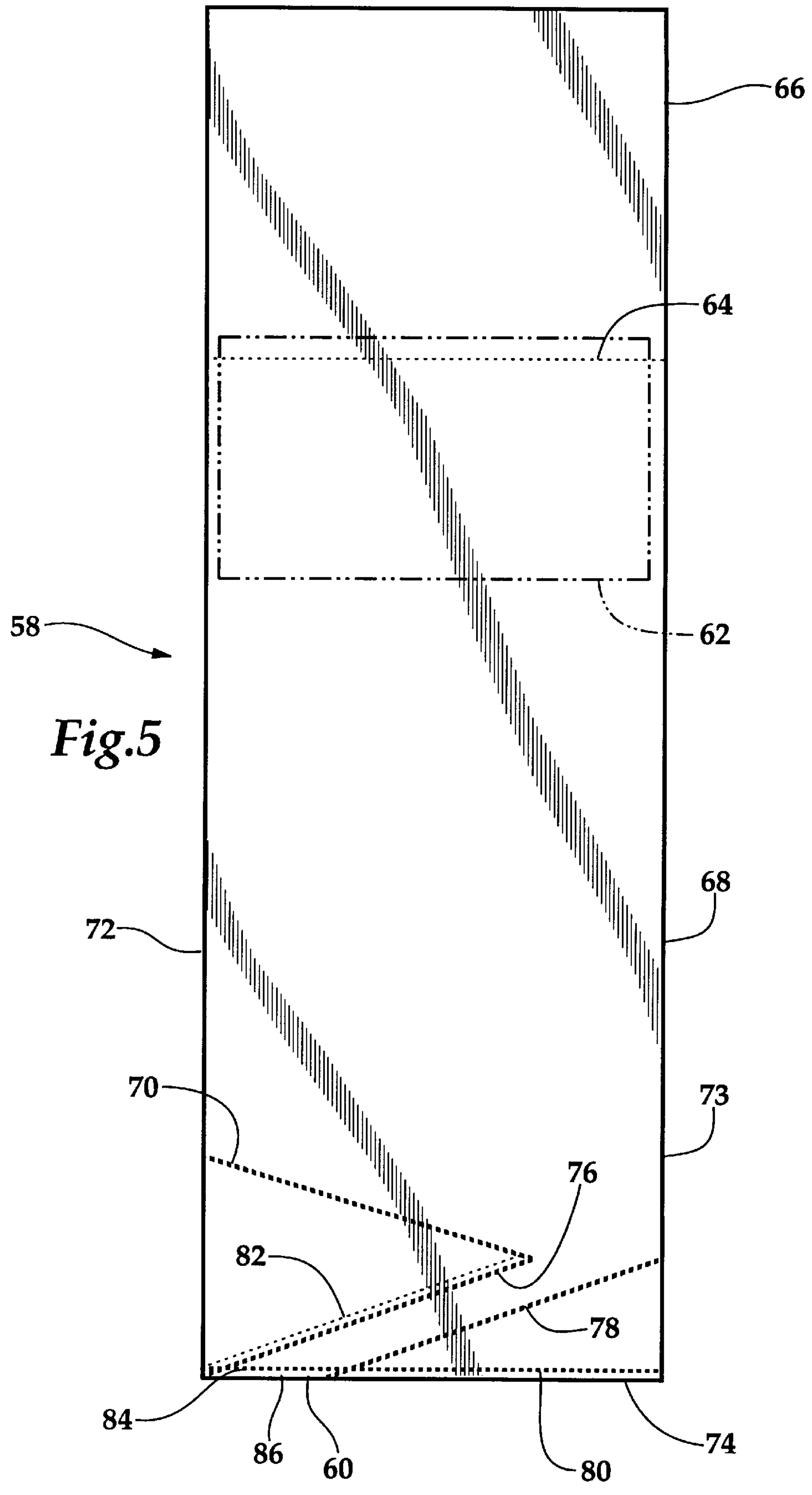
FIG. 5 is a plan view of an alternative embodiment boar semen collection bag of this invention having an integral dispensing segment.

An alternative embodiment boar semen collection bag 58, shown in FIG. 5, is provided with an integral dispensing segment 60 which enables a smaller operation to conveniently transfer the collected and extended semen directly from the collection bag 58 to smaller containers. The bag 58 permits an operation that may only be collecting from one or two boars a week to transfer the collected semen to the conventional 100 ml or 3 fluid oz plastic bottles without the need for automatic equipment.

The bag 58 has a filter element 62 attached to the bag above a perforated line 64 which divides the disposable portion of the bag 66 from the collection portion of the bag 68. The bag 58 is preferably formed from a roll of tubular plastic, with the side wall of the bag 58 thus being continuous, thereby eliminating the need to seal any side seams on the bag. The tubular plastic comes off the roll flat, with two side walls of the bag positioned parallel, one above the other, to thereby define parallel side edges 72, 73. The filter element 62 is formed and attached to the disposable portion 66 of the bag in the same manner as discussed with respect to the bag 20 above. The dispensing segment 60 is formed from portions of the collection portion 68 itself by a first heat seal line 70 which extends at an angle from a first side edge 72 toward the bottom 74 of the bag and toward the opposite side edge 73. The heat seal line 70 terminates prior to reaching the opposite side edge 73 of the bag, and it meets an upper spout heat seal line 76 which extends back toward the first side edge 72. The upper spout heat seal line 76 extends toward and intersects the bottom 74 of the bag. A lower spout heat seal line 78 extends from the second side edge 73 at approximately the level at which the heat seal line 70 terminates. The lower spout heat seal line 78 extends from the second side edge 73 to the bottom 74 of the bag, and terminates spaced horizontally from the termination of the upper spout heat seal line 76. The bottom 74 is sealed by a horizontal bottom heat seal line 80 which extends across the dispensing segment 60.

A perforation line 82 extends parallel to and above the upper spout heat seal line 76. This perforation line may also be any other weakened region of material, including, for example, forming a thinner region of plastic colinear with the heat seal 76 in the heat sealing process. During the collection of the semen from the boar, the dispensing segment 60 of the bag will be retained folded over at the bottom of the collection mug. When the extender has been added to the neat semen, and the operator is ready to dispense the extended semen into smaller containers, the upper edges of the collection portion 68 of the bag may be elevated and clamped in place on a simple fixture such as two clips fastened to a cabinet. Any appropriate means for mounting the filled bag may alternatively be employed. For example, the upper regions of the collection bag may be tied into a knot, and hooked over a nail or hook, or a cable tie may be looped around the knot, and the cable tie hooked over the nail.

To dispense the bag contents, the operator tears along the perforation line 82 to free the upper edge of the spout 84, and allow the spout to be pivoted downward from the main body of the bag. Using a scissors, the tip of the spout 84 is cut off to form a dispensing opening 86 in the spout. This dispensing opening 86 is preferably formed to be narrower than the conventional inlet diameter of the packaging container into which the semen is to be discharged. Once the spout has been opened, the operator may close the spout by pressing it between his thumb and index finger, or if the spout is to be left unattended, the spout may be folded over and tied or clamped, for example with a spring clamp, a rubber band or the like.

It should be noted that the spout may be folded up and temporarily affixed to the bag in such a way to prevent the admission of semen into the spout until such time as the operator is ready to dispense the extended semen. Nevertheless, in cost sensitive applications, this step may be omitted. Instead, the operator may use care in collecting the semen to fold the bottom portions of the collection bag when the bag is positioned within the collection mug so that semen does not enter the spout during the collection process. The lower portions of the bag may then be kept folded over until the extender has been added and thoroughly mixed with the semen. Even in the event that neat semen finds its way into the spout, the extender may still be evenly mixed with the semen in the spout by grasping the exterior of the bag along the spout and massaging the bag to introduce extender into the spout, prior to opening the spout outlet.

It should be noted that the boar semen collection bag of this invention may be constructed of materials other than specific ones discussed above, and that the region of weakened material may be formed by other than the mechanical perforations discussed. In addition, the bag and the filter element may be formed as other than rectangular in shape.

It is understood that the invention is not limited to the particular construction and arrangement of parts herein illustrated and described, but embraces such modified forms thereof as come within the scope of the following claims.

I claim:

1. A receptacle for the collection of boar semen comprising:

an upwardly opening bag comprised of a first segment overlying a second segment, the two segments being connected together along the bottom and the sides of the bag;

portions of the bag comprising a region of weakened material which encircles the bag and extends across both the first segment and the second segment, the region of weakened material defining a line of separation which divides the bag into a collection portion and a disposable portion, the region of weakened material permitting the disposable portion to be separated from the collection portion; and a filter material positioned within the bag, the filter material being fastened to the disposable portion of the bag upwardly of the region of weakened material, the bag being extendable from a first flattened condition in which the filter material extends substantially parallel to the bag first segment and the bag second segment, and a collection condition, in which the bag is spread such that the filter material extends inwardly from the bag first segment and the bag second segment, such that boar ejaculate may be received on the filter material and the boar semen component of the ejaculate may pass through the filter into the collection portion of the bag, the disposable portion with the attached filter and uncollected ejaculate component being separable from the collection portion of the bag and the contained semen component.

2. The receptacle of claim 1 wherein the filter material comprises a single rectangular sheet which is folded to have two upper edges, the upper edges being fixed to the bag upwardly of the region of weakened material.

3. The receptacle of claim 2 wherein the filter material has two spaced sides, and each side is fused to itself, to define an upwardly opening filter pouch.

4. The receptacle of claim 1 wherein the bag first segment and the bag second segment are formed from a tubular section of plastic.

5. The receptacle of claim 1 further comprising:

a lower seam which extends between a first side and a second side of the bag;

a first seam which extends from the bag first side part way toward the bag second side, wherein the first bag segment is fused to the second bag segment at the first seam;

a second seam which extends from the first seam to the bag lower seam at a position adjacent the bag first side;

a third seam which extends from the bag second side to the bag lower seam, the third seam terminating at a position spaced from the second seam; and portions of the bag approximately parallel to the first seam which define a region of weakened material, such that the portions of the bag below the first seam may be moved away from the portions of the bag above the first seam to define a movable spout for the discharge of contents from the receptacle.

6. A boar semen collection assembly, comprising:

an upwardly opening bag having a first segment which overlies a second segment, the two segments being connected along a first side and a second side, the first side being spaced from the second side;

portions of the bag comprising a region of weakened material which encircles the bag and extends across both the first segment and the second segment, the region of weakened material defining a line of separation which divides the bag into a collection portion and a disposable portion, the region of weakened material permitting the disposable portion to be separated from the collection portion; and an upwardly opening filter pouch enclosed within the bag, wherein the filter pouch is fastened to the disposable portion of the bag upwardly of the region of weakened material, and wherein the bag is extendable from a flattened condition to a collection condition, in which the bag is spread such that the filter pouch extends inwardly from the bag first segment and the bag second segment, such that boar ejaculate may be received on the filter material and the boar semen component of the ejaculate may pass through the filter into the collection portion of the bag, the disposable portion with the attached filter and uncollected ejaculate component being separable from the collection portion of the bag and the contained semen component.

7. The boar semen collection assembly of claim 6 wherein the filter pouch comprises:

a first rectangular section having an upper edge; and a second rectangular section having an upper edge and connected to the first rectangular section along two side seams and a bottom line, the upper edges of the pouch rectangular sections being fixed to the bag upwardly of the region of weakened material.

8. The boar semen collection assembly of claim 6 wherein the bag first segment and the bag second segment are formed from a tubular section of plastic.

9. The boar semen collection assembly of claim 6 further comprising:

a lower seam which extends between the first side and the second side of the bag;

a first seam which extends from the bag first side part way toward the bag second side, wherein the first bag segment is fused to the second bag segment at the first seam;

a second seam which extends from the first seam to the bag lower seam at a position adjacent the bag first side;

a third seam which extends from the bag second side to the bag lower seam, the third seam terminating at a position spaced from the second seam; and portions of the bag approximately parallel to the first seam which define a region of weakened material, such that the portions of the bag below the first seam may be moved away from the portions of the bag above the first seam to define a movable spout for the discharge of contents from the receptacle.

10. An apparatus for the collection, storage, and dispensing of boar semen, comprising:

an upwardly opening collection bag;

a filter element fixed to portions of the collection bag and enclosed within the collection bag; and portions of the bag which define a spout positioned below the filter element, the spout being sealed in a closed condition when semen is being received within the collection bag, and the spout being movable with respect to the collection bag to discharge the contents of the collection bag into a container, and wherein portions of the bag to which the filter element is fixed are separable from portions of the bag beneath the filter element, to permit collected boar semen within the collection bag to be separated from the filter element.

11. The apparatus of claim 10 wherein the filter element comprises a sheet of filter material which is folded over on itself and sealed along two opposed sides to define an upwardly opening filter pouch.

12. The apparatus of claim 11 wherein the filter pouch has two spaced upper edges which are fused to the collection bag along a region of weakened material, such that the filter pouch can be torn cleanly from the collection bag after the boar semen has been collected.

13. The apparatus of claim 10 wherein the spout is defined by portions of the collection bag comprising:

a lower seam which extends between a first side and a second side of the bag;

a first seam which extends from the bag first side part way toward the bag second side, wherein the first bag segment is fused to the second bag segment at the first seam;

a second seam which extends from the first seam to the bag lower seam at a position adjacent the bag first side;

a third seam which extends from the bag second side to the bag lower seam, the third seam terminating at a position spaced from the second seam; and portions of the bag approximately parallel to the first seam which define a region of weakened material, such that the portions of the bag below the first seam may be moved away from the portions of the bag above the first seam to define the spout for the discharge of contents from the receptacle.

* * * * *